(12) United States Patent
Thiele et al.

(10) Patent No.: US 8,038,618 B2
(45) Date of Patent: *Oct. 18, 2011

(54) ULTRASOUND-IMAGING SYSTEMS AND METHODS FOR A USER-GUIDED THREE-DIMENSIONAL VOLUME-SCAN SEQUENCE

(75) Inventors: Karl Erhard Thiele, Andover, MA (US); Rodney J. Solomon, Andover, MA (US); George Adleman, Arlington, MA (US); Bernard Savord, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/423,032

(22) Filed: Apr. 14, 2009

(65) Prior Publication Data
US 2009/0203996 A1 Aug. 13, 2009

Related U.S. Application Data

(62) Division of application No. 10/254,130, filed on Nov. 15, 2002, now Pat. No. 7,758,508.

(51) Int. Cl.
*A61B 8/00* (2006.01)
(52) U.S. Cl. .............................. 600/443; 600/440
(58) Field of Classification Search ............ 600/437; 128/916
See application file for complete search history.

(56) References Cited

U.S. PATENT DOCUMENTS

| | | | |
|---|---|---|---|
| 6,167,296 A * | 12/2000 | Shahidi | 600/427 |
| 6,174,285 B1 | 1/2001 | Clark | |
| 6,186,948 B1 | 2/2001 | Kamiyama et al. | |
| 6,245,017 B1 | 6/2001 | Abe et al. | |
| 6,374,674 B1 | 4/2002 | Mine | |
| 6,690,371 B1 * | 2/2004 | Okerlund et al. | 345/424 |
| 7,758,508 B1 * | 7/2010 | Thiele et al. | 600/447 |
| 2003/0156746 A1 | 8/2003 | Bissell et al. | |

FOREIGN PATENT DOCUMENTS

| | | |
|---|---|---|
| EP | 1419737 A | 5/2004 |
| JP | 2000287976 A | 10/2000 |
| WO | 03045222 A | 6/2003 |
| WO | 2004029655 A | 4/2004 |

* cited by examiner

*Primary Examiner* — Michael Rozanski
(74) *Attorney, Agent, or Firm* — W. Brinton Yorks, Jr.

(57) ABSTRACT

An ultrasound-imaging system and method is provided that permits an operator to acquire an image of a volume-of-interest in a time critical fashion, that is capable of referencing the volume rendering to a standard two-dimensional imaging mode, and permits the operator to selectively choose a number of display-mode parameters that result in an operator directed view of the volume-of-interest. The ultrasound-imaging system comprises an input device configured to receive a plurality of imaging parameters and a controller in communication with the input device. The ultrasound-imaging system generates an operator-directed transmit-beam scan sequence in response to the imaging parameters and transmits a spatially modified transmit-beam scan sequence over a portion of the volume-scan range of the ultrasound-imaging system. Moreover, the ultrasound-imaging system provides the flexibility for an operator to direct a plurality of operator-configurable multi-dimensional views.

8 Claims, 10 Drawing Sheets

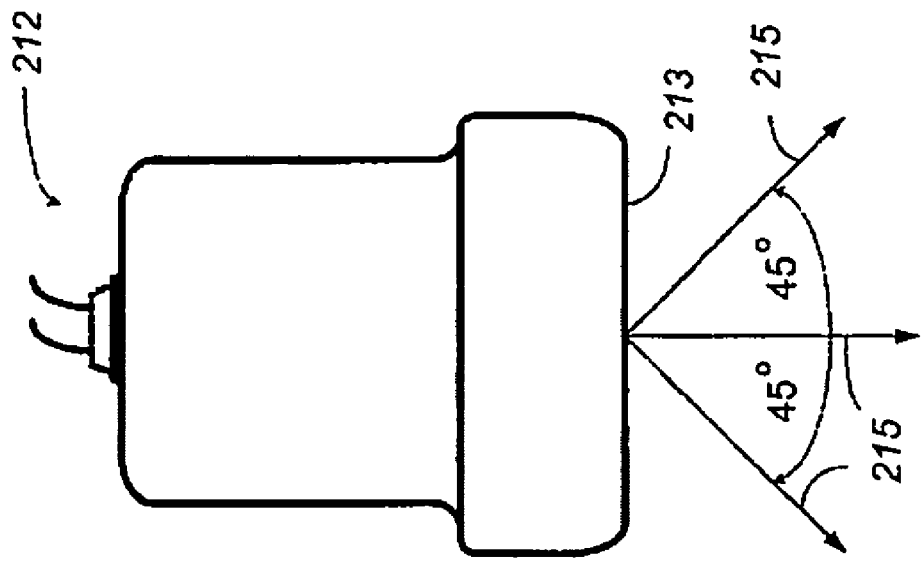

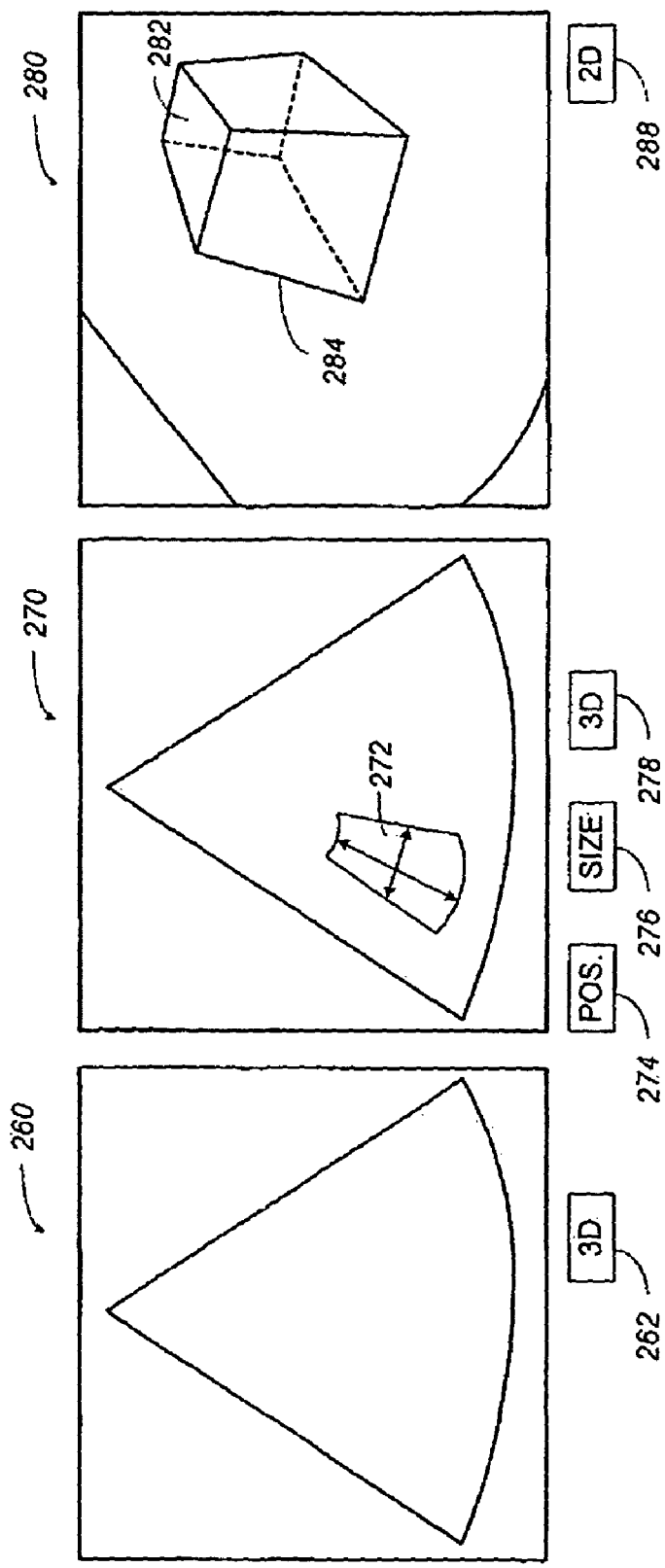

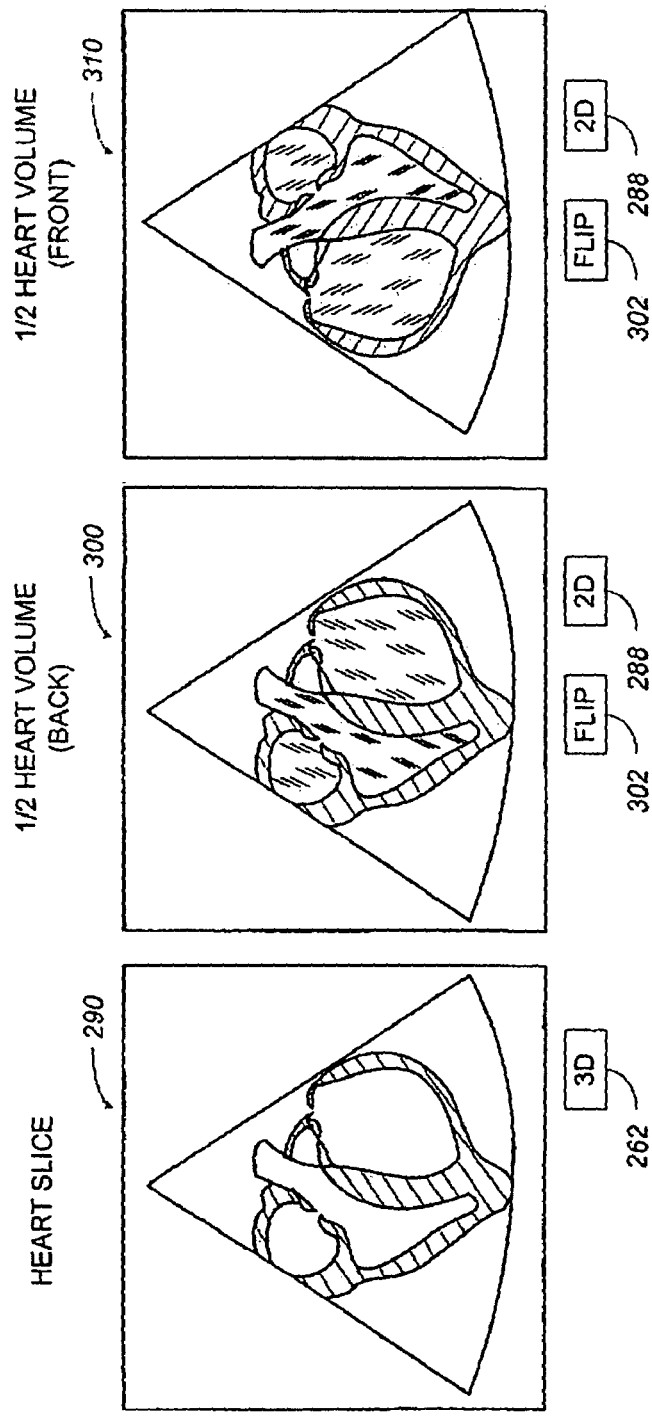

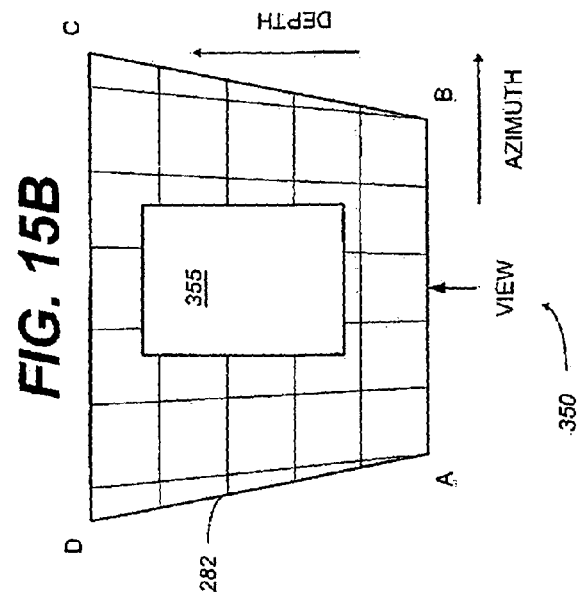
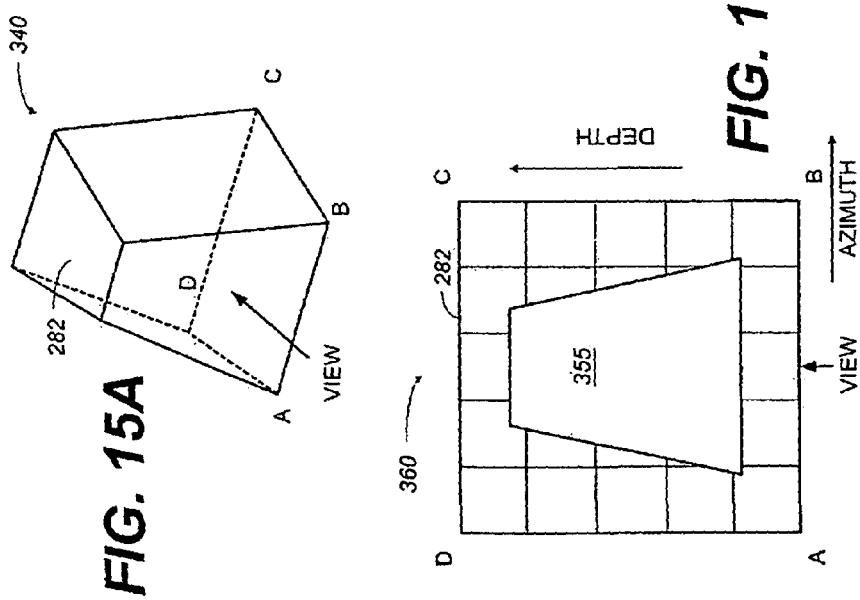

ULTRASOUND-IMAGING SYSTEMS AND METHODS FOR A USER-GUIDED THREE-DIMENSIONAL VOLUME-SCAN SEQUENCE

This is a divisional patent application of U.S. patent application Ser. No. 10/254,130, filed Nov. 15, 2002 which is now U.S. Pat. No. 7,758,508.

FIELD OF THE INVENTION

The present invention generally relates to three-dimensional ultrasound-imaging systems for the purpose of medical diagnosis, and more particularly, to an improved three-dimensional ultrasound-imaging system and method that provides an increased frame rate or an optimized image-acquisition time.

BACKGROUND OF THE INVENTION

Ultrasonic imaging has become an important and popular diagnostic tool with a wide range of applications. Particularly, due to its non-invasive and typically non-destructive nature, ultrasound imaging has been used extensively in the medical profession. Modern high-performance ultrasound-imaging systems and techniques are commonly used to produce both two-dimensional and three-dimensional diagnostic images of internal features of an object, (e.g., portions of the anatomy of a human patient). A diagnostic ultrasound-imaging system generally uses a wide-bandwidth transducer to emit and receive ultrasound signals. The ultrasound-imaging system forms images of the internal tissues of a human body by electrically exciting an acoustic-transducer element or an array of acoustic-transducer elements to generate ultrasonic pulses that travel into the body. The ultrasonic pulses produce echoes as they reflect off of body tissues that appear as discontinuities to the propagating ultrasonic pulses. The various echoes return to the transducer and are converted into electrical signals that are amplified and processed to produce an image of the tissues. These ultrasonic-imaging systems are of significant importance to the medical field by providing physicians real-time high-resolution images of internal features of a human anatomy without resort to more invasive exploratory techniques such as surgery.

As described above, ultrasonic-imaging systems employ an acoustic transducer to radiate and receive a plurality of ultrasonic pulses. The acoustic transducer, which radiates the ultrasonic pulses, typically comprises a piezoelectric element or an array of piezoelectric elements. As is known in the art, a piezoelectric element deforms upon application of an electrical signal to produce the transmitted ultrasonic pulses. Similarly, the received echoes cause the piezoelectric element to deform and generate a corresponding receive-electrical signal. The acoustic transducer is often packaged in a hand-held device that allows an operator substantial freedom to manipulate the transducer over a desired area of interest. The transducer is often connected via a cable to a control device that generates and processes the electrical signals. In turn, the control device may transmit image information to a real-time viewing device, such as a monitor. In alternative configurations, the image information may also be transmitted to physicians at a remote location and or stored to permit viewing of the diagnostic images at a later time.

To generate a three-dimensional image, volumetrically spaced information, such as planar or line information, associated with positional information is obtained by using any of various transducers. One approach is to use a two-dimensional transducer array to obtain three-dimensional image information directly. A two-dimensional array can be used to scan electronically in any desired orientation to acquire the desired information. Another approach is to collect multiple two-dimensional image data frames using a one-dimensional or a 1.5 dimensional transducer array along with relative positional information associated with the image-data frames so that these frames may be sequentially assembled in a three-dimensional volume to form the desired three-dimensional reconstruction.

Based on echo signals received from the transducer, as described above, the volumetric information, such as assembled from multiple sets of planar information, is generated. The image information is derived as a function of various imaging modes. For example, B-mode or brightness mode, or color-Doppler image mode.

Once the volumetrically spaced information, such as planar information, and associated-positional information is provided, standard methods are employed for assembling the image information into a three-dimensional volume of the subject and for providing the desired display, such as a cross-section, a surface rendering, or the like.

Some prior-art ultrasound-imaging systems were designed with the philosophy that a technician would perform the task of acquiring a "full volume" of an organ of interest within a patient and that a physician or other clinician would review the results of a diagnostic session providing a plurality of images offline. Under this diagnostic modality, it is imperative that the technician obtains all of the slices and projections necessary for a diagnosis. As a result, no provisions were provided to permit the technician to reduce the size of a volume-under-observation (VUO).

However, it takes a considerable amount of time to acquire a large volume scan, which negatively impacts the frame rate in a real-time imaging system. In non-real-time systems, it is the total time of acquisition that is negatively impacted. For example, it may take upwards of 5 minutes to acquire a full four-dimensional (space and time) volume of the human heart over a single cardiac cycle.

Some prior-art imaging systems addressed the issue of frame rate by incorporating a multi-channel parallel beam-formation structure within the hardware. However, this approach significantly increases the cost and the size of the resulting ultrasound-imaging system. A multi-channel parallel beamforming hardware solution is illustrated in FIG. 1. As shown, a prior-art three-dimensional imaging system 10 may comprise a transmit controller 12, a transducer 14, a parallel configuration of receive beamformers 16a, 16b, 16c, . . . , 16x, a radio frequency (RF) filter 18, both a Doppler-image processor 20 and a B-mode image processor 22. The prior-art three-dimensional imaging system 10 may further comprise a scan converter 24, a three-dimensional image processor 26, an image-data storage device 28, and a display 30.

As illustrated in FIG. 1, the prior art three-dimensional imaging system 10 may use a transmit controller 12 to control the operation and timing of multiple excitation signals that may be forwarded to the transducer 14. The transducer 14 may be configured to emit and receive-ultrasound signals, or acoustic energy, respectively to and from an object-under-test (not shown). In response to ultrasound-transmit signals, one or more echoes are emitted by the object-under-test and are received by the transducer 14, which transforms the echoes into an electrical signal for further processing. During a receive mode, an analog waveform is received at the transducer 14 at a number of beam positions. Each of the plurality of received analog waveforms may be forwarded to a dedicated receive beamformer 16a through 16x. Each of the set of parallel beamformers 16 may receive a series of analog waveform sets, one set for each separate acoustic line, in succession over time and may process the waveforms in a pipeline-processing manner. Each of the set of parallel beamformers 16a through 16x may be configured to convert its respective analog-echo waveform into a digital-echo waveform comprising a number of discrete-location points. Each of the set of parallel beamformers 16a through 16x may delay the separate echo waveforms by different amounts of time and then may add the delayed waveforms together, to create a composite-digital RF-acoustic line.

A RF filter 18 may be coupled to the output of the parallel beamformers 16 and may be configured to receive and process digital-acoustic lines in succession. The RF filter 18 may be in the form of a bandpass filter. As further illustrated in FIG. 1, the filtered image data may be forwarded to a Doppler image processor 20 and a B-mode image processor 22 for two-dimensional image mode processing. As further illustrated in FIG. 1, the Doppler-image processor 20 and the B-mode image processor 22 may be coupled to a scan converter 24 to convert the image data into a format suitable for display. The scan converter 24 may process the data once an entire data frame (i.e., a set of all acoustic lines in a single view, or image/picture to be displayed) has been accumulated.

Next, the prior-art three-dimensional imaging system 10 may forward the converted image data to a three dimensional image processor 26 for performing the necessary mathematical manipulations to generate volumetric information from a series of planar (i.e., two-dimensional) ultrasound images. As further illustrated in FIG. 1, the three-dimensional image processor 26 may be coupled to an image-data storage device 28 and a display 30. The image data storage device 28 may permit both still frame and video image storage for offline-image manipulation and viewing. The display 30 may take the form of a specialized cathode-ray-tube (CRT) or other suitable image-creating device that may permit real-time image viewing by an operator.

As previously described, volumetric information consisting of multiple planes, may be collected by a prior-art three-dimensional imaging system 10 (FIG. 1) as illustrated in FIG. 2. For example, the planar information 40 may be collected by using the transducer 14 to transmit a plurality of ultrasonic-transmit planes 13a, 13b, 13c, . . . , 13f as shown. The plurality of transmit planes 13 may generate a plurality of response planes (not shown) that may be received by the transducer 14. The plurality of response planes, together with positional information, may be processed by the prior-art three-dimensional imaging system 10 of FIG. 1 to generate a three-dimensional image. As further illustrated in FIG. 2, volumetric information may be scanned over a 60° by 60° footprint at a depth of 16 cm. As also illustrated in FIG. 2, the plurality of response planes 13 may span a length and a width of 16 cm, thus forming a volumetric information pyramid. As is evident by observing FIG. 2, a VUO (e.g., an organ or a portion of an organ of the human anatomy) must lie within the three-dimensional "scan" pyramid formed by the plurality of ultrasonic transmit planes 13. The planar information 40 collected by the prior art three-dimensional imaging system 10 (FIG. 1) as illustrated in FIG. 2 is representative of planar information 40 that may be collected with a stationary transducer 14.

To achieve a large volume (60°×60°) in real-time (i.e., better than 15 Hz), the prior-art three-dimensional imaging system 10 (FIG. 1) was forced to use 16x parallel beamformers. This 16x parallel beamformer architecture is undesirable as the realizable three-dimensional resolution comes at a significant cost, especially when compared with prior art two-dimensional imaging systems. First, the cost for each beamformer makes the prior art three-dimensional imaging system relatively expensive. Second, to achieve 16x parallel (1 transmit firing for 16 simultaneous receive acquisitions) operation, the prior art three-dimensional imaging system 10 uses a broadened transmit beam of approximately 4°×4°. Then within the transmit beamwidth, 16 receive beams (each 1° apart) are interrogated using a 4°×4° receive beamwidth. The "round-trip" resolution is effectively a multiplication of the transmit and the receive beamwidths. As a result, of the relatively broad-transmit and interrogation beamwidths, the prior-art three-dimensional imaging system 10 loses significant resolution when compared to prior-art two-dimensional only imaging systems.

Other prior art systems have been devised that use various devices to control the relative position of the transducer 14 with respect to a VUO. It will be appreciated that planar information 40 may be collected by a three dimensional imaging system configured to vary the position of the transducer 14. The planar information 40 resulting from a plurality of two-dimensional views acquired with a position-varying transducer may take the form of slices. In return for increased complexity, ultrasound-imaging systems capable of varying the relative position of the transducer 14 can acquire a larger volume than those systems that use a fixed-position transducer 14. Regardless of the two-dimensional imaging methodology selected, appropriate algorithms are known for combining the image information with positional information associated with each of the image slices acquired to develop a three-dimensional rendering of a VUO.

Having generally described two prior art methods for acquiring a three-dimensional volume using a plurality of two-dimensional images, reference is now directed to FIG. 3, which illustrates prior-art performance characteristics that may be expected using a relatively large beamwidth and a multi-channel parallel-beamforming system.

In this regard, FIG. 3 further describes the operation of the prior-art three-dimensional imaging system 10 of FIG. 1. More specifically, FIG. 3 illustrates a plot of expected-performance characteristics 50 such as transmit plane 52, receive plane 54, and round-trip 56 sensitivity versus transmitted beamwidth as may be expected with the prior-art three-dimensional imaging system 10. FIG. 3 will be further discussed in relation to the plot of FIG. 6 where a comparison will be made with expected performance characteristics for a three-dimensional imaging system in accordance with the present invention.

In addition, to the increased cost and size of various prior-art ultrasound-imaging systems, another problem associated with acquiring full volumes is that the target volume's location is referenced to the probe. As a result, references to the anatomy must be translated accurately to accurately identify and diagnose a tissue volume under observation. References to the anatomy are typically minimal and either involve technician "labeling" or relying on the diagnosing clinician to identify the anatomy. As such, it often becomes difficult for the reviewing clinician to understand what they are looking at. Unless they are very skilled and experienced with a particular-imaging system and typical images that are produced, the clinician often becomes "lost in the volume."

As a result, there is a need for an improved four-dimensional (space and time) ultrasound-imaging system that permits an operator to acquire a volume in a time-critical fashion, that is capable of referencing the volume rendering to a standard two-dimensional imaging mode, and permits the operator to selectively choose a number of display-mode parameters that result in a user-directed view within a VUO.

SUMMARY OF THE INVENTION

The present invention provides an ultrasound-imaging system and method for acquiring a user-identified target volume in a time-efficient manner. An operator interacting with the ultrasound-imaging system identifies the volumetric size, the location, the view angle, etc. of a target volume. In response to the operator input, the ultrasound-imaging system may alter a scan sequence, an acoustic-line direction, and an acoustic-line spacing to acquire a three-dimensional image in a time-efficient manner. The operator can significantly influence the rate of target-volume acquisition by trading off the size of the volume selected, the frame rate, and the desired resolution. By permitting an operator to position a variable-sized target volume-of-interest (VOI) (i.e., not necessarily the entire organ) within a volume-under-observation (VUO), which may comprise any volume larger than the VOI, frame rates can be optimized. This optimization results from the firing of acoustic lines in the desired VOI versus a larger target volume (e.g., a volume under observation or VUO).

The ultrasound-imaging system may reference the target volume (i.e., the VOI) in both position and size in reference to a standard two-dimensional image mode (e.g., a B-mode or a Doppler color-flow image mode). As a direct result, the target volume can be specified by an operator using a standard two-dimensional imaging mode as a primary reference. In addition, the two-dimensional reference image information can be acquired in real-time and later displayed along with the desired VOI to provide a recognizable reference to a clinician (e.g., a physician).

The ultrasound-imaging system may vary the periodicity of the transmitted acoustic lines (e.g., the angular distance between subsequent acoustic lines may vary spatially). These differences in spatial density may be influenced by operator inputs, where the variations in spatial-line density are used to minimize acoustic-echo acquisition time or to optimize resolution in specific regions of the target volume. In one mode, after identifying a preferred-viewing angle, acoustic lines closest to the view source (or camera position) would have a higher density. As the distance away from the view source increases, the ultrasound-imaging system may produce transmit-acoustic lines further and further apart. One benefit of varying the acoustic transmit-line spacing is that subsequent algorithmic processing can be facilitated. In specific cases, it is possible to incorporate perspective into the three-dimensional image by changing the spacing of the transmit-acoustic lines. One way this may be accomplished is by reducing the spacing of transmit lines (and resolution along the lines) as their distance from a user-identified view window increases. After the ultrasound-echo information is acquired, image perspective may be introduced by displaying the image data using a spacing more uniform with distance from a user-selectable view window. Yet another benefit associated with the ultrasound-imaging system of the present invention is that subsequent scan conversion may be facilitated by firing acoustic lines using a user-identified frustum within the VUO as a frame of reference.

Architecturally, an ultrasound-imaging system in accordance with the present invention may include a transducer in electrical communication with an ultrasound-system controller configured to generate and forward a series of ultrasound-energy pulses to the transducer. The ultrasound-system-controller is further configured to receive and recover information from ultrasound-target echoes for further processing by any number of devices capable of translating the recovered ultrasound target-echo information into a viewable three-dimensional image. For example, an ultrasound-imaging system in accordance with the present invention may comprise a transducer, an ultrasound-electronics system, and a display-electronics system. The ultrasound-electronics system may comprise a transmit controller, a receive beamformer, a system controller, a plurality of filters, a plurality of two-dimensional image mode processors, and a scan converter. The display electronics may comprise both two-dimensional and three-dimensional image processors, an image-memory device, and a display.

The present invention may also be broadly viewed as providing a method for ultrasound imaging. Briefly stated, the method comprises the following steps: prompting a user for a plurality of user-selectable inputs to identify a region-of-interest within a larger volume under observation; adjusting a plurality of ultrasound-imaging parameters in response to the plurality of user-selectable inputs; transmitting a plurality of scan lines in accordance with the ultrasound-imaging parameters; recovering a plurality of scan-line generated responses; and deriving a three-dimensional image of the region-under-test with a user-selectable option to overlay a standard two-dimensional display-mode image.

Other features and advantages of the invention will become apparent to one with skill in the art upon examination of the following drawings and detailed description. These additional features and advantages are intended to be included herein within the scope of the present invention.

BRIEF DESCRIPTION OF THE DRAWINGS

FIG. 6 is a plot illustrating transmit and receive ultrasound-signal sensitivity versus beamwidth as may be attained by the three-dimensional ultrasound-imaging system of FIG. 4.

FIG. 7 is a schematic side view of a transducer that may be coupled to the ultrasound-electronics system of FIG. 4 to generate a plurality of steered transmit beams.

FIGS. 8-13 are schematic views of possible ultrasound-imaging displays (i.e., modes) that may be generated by the three-dimensional ultrasound imaging system of FIG. 4.

FIGS. 15A through 15C introduce a perspective view and two plots illustrating an operator-selectable view-point and the varying of transmit-scan lines to simulate perspective as may be implemented by the three-dimensional ultrasound-imaging system of FIG. 4.

DETAILED DESCRIPTION

The three-dimensional ultrasound-imaging system and method of the present invention will now be specifically described in detail in the context of an ultrasound-imaging system that creates and displays brightness-mode (B-Mode) images, or gray-scale images, as well as, color-flow or Doppler-mode images which are well known. However, it should be noted that the teachings consistent with the improved three-dimensional ultrasound-imaging system and method of the present invention may be practiced using other ultrasound-imaging systems that are suited for the method, as will be apparent to those skilled in the art.

System Architecture and Operation

Figure 4:
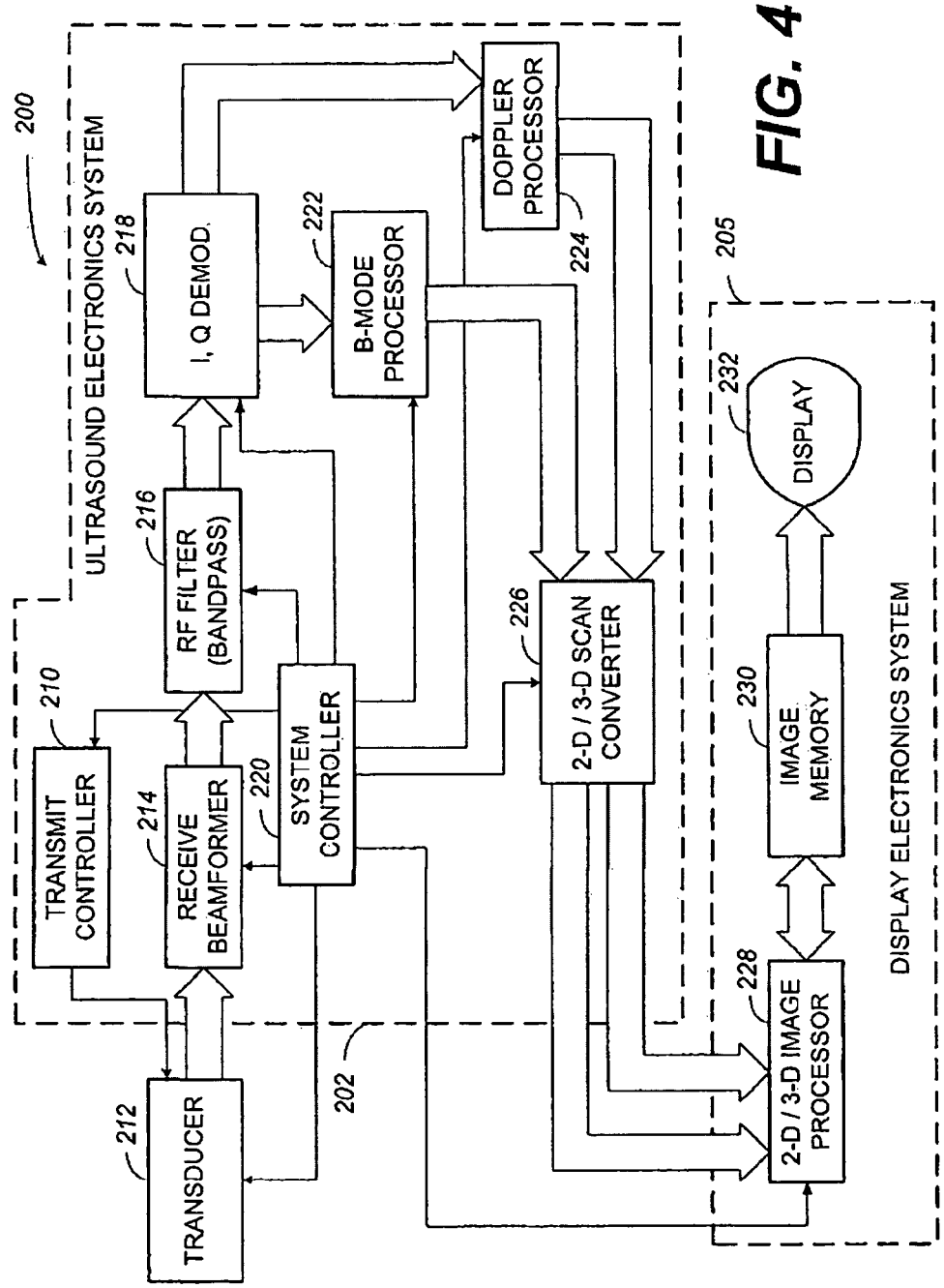
FIG. 4 is a block diagram illustrating an embodiment of a three-dimensional ultrasound-imaging system in accordance with the present invention.

An exemplar architecture of an embodiment of an ultrasound-imaging system capable of implementing the method of the present invention is illustrated by way of a functional block diagram in FIG. 4 and is generally denoted by reference numeral 200. Note that many of the functional blocks illustrated in FIG. 4 define a logical function that can be implemented in hardware, software, or a combination thereof. For purposes of achieving high speed, it is preferred, at present, that most of the blocks be implemented in hardware, unless specifically noted hereafter.

Referring to FIG. 4, an ultrasound-imaging system 200 may include an ultrasound-electronics system 202 in communication with a transducer 212 and a display-electronics system 205. As illustrated in FIG. 4, the ultrasound-electronics system 202 may include a system controller 220 designed to control the operation and timing of the various elements and signal flows within the ultrasound-imaging system 200 pursuant to suitable software. The ultrasound-electronics system 202 may further comprise a transmit controller 210, a receive beamformer 214, a radio-frequency (RF) (bandpass) filter 216, an I, Q demodulator 218, a B-mode processor 222, a Doppler processor 224, and a two-dimensional/three-dimensional scan converter 226. As further illustrated in FIG. 1, the display-electronics system 205 may comprise a two-dimensional/three-dimensional image processor 228, an image memory 230, and a display 232.

The transducer 212 may be configured to emit and receive ultrasound signals, or acoustic energy, respectively to and from an object-under-test (e.g., the anatomy of a patient when the ultrasound-imaging system 200 is used in the context of a medical application). The transducer 212 is preferably a phased-array transducer having a plurality of elements both in the azimuth and elevation directions.

In one embodiment, the transducer 212 comprises an array of elements typically made of a piezoelectric material, for example but not limited to, lead-zirconate-titanate (PZT). Each element is supplied with an electrical pulse or other suitable electrical waveform, causing the elements to collectively propagate an ultrasound-pressure wave into the object-under-test. Moreover, in response thereto, one or more echoes are emitted by the object-under-test and are received by the transducer 212, which transforms the echoes into an electrical signal for further processing.

The array of elements associated with the transducer 212 enable a beam, emanating from the transducer array, to be steered (during transmit and receive modes) through the object by shifting the phase (introducing a time delay) of the electrical pulses/biasing signals supplied to the separate transducer elements. During a transmit mode, an analog waveform is communicated to each transducer element, thereby causing a pulse to be selectively propagated in a particular direction, like a beam, through the object.

During a receive mode, an analog waveform is received at each transducer element at each beam position. Each analog waveform essentially represents a succession of echoes received by the transducer element over a period of time as echoes are received along the single beam through the object. The entire set of analog waveforms represents an acoustic line, and the entire set of acoustic lines represents a single view, or image, of an object and is referred to as a frame.

A transmit controller 210 may be electrically connected to the transducer 212. The transmit controller 210 may be in furthercommunication with the system controller 220. The system controller 220 may be configured to send one or more control signals to direct operation of the transmit controller 210. In response, the transmit controller 210 may generate a series of electrical pulses that may be periodically communicated to a portion of the array of elements of the transducer 212, causing the transducer elements to emit ultrasound signals into the object-under-test of the nature described previously. The transmit controller 210 typically provides separation (in time) between the pulsed transmissions to enable the transducer 212 to receive echoes from the object during the period between pulsed transmissions and forwards the received echoes to a set of parallel channels within the receive beamformer 214.

The receive beamformer 214 may receive a series of analog electrical-echo waveforms from the transducer 212 that are generated by echoes emitted from the object-under-test. More specifically, the receive beamformer 214 may receive an analog electrical-echo waveform from a corresponding transducer element for each acoustic line. Moreover, the receive beamformer 214 may receive a series of waveform sets, one set for each separate acoustic line, in succession over time and may process the waveforms in a pipeline-processing manner. Because the ultrasound signals received by the transducer 212 are of low power, a set of preamplifiers that may be disposed within the receive beamformer 214 should be of sufficient quality that excessive noise is not generated in the amplification process.

Because the echo waveforms typically decay in amplitude as they are received from progressively deeper depths in the object-under-test, the receive beamformer 214 may further comprise a parallel plurality of time-gain compensators (TGCs—not shown), which are designed to progressively increase the gain along the length of each acoustic line, thereby reducing the dynamic range requirements on subsequent processing stages. Moreover, the set of TGCs 22 may receive a series of waveform sets, one set for each separate acoustic line, in succession over time and may process the waveforms in a pipeline-processing manner.

The receive beamformer 214 may also comprise a plurality of parallel analog-to-digital converters (ADCs—not shown) which may be in communication respectively with a plurality of channel dedicated TGCs. Each of the ADCs in the receive beamformer 214 may be configured to convert its respective analog-echo waveform into a digital-echo waveform comprising a number of discrete-location points (hundreds to thousands; corresponding with depth and may be a function of ultrasound-transmit frequency) with respective quantized instantaneous signal levels, as is well known in the art. In previous prior-art ultrasound-imaging systems, this conversion often occurred later in the signal processing steps, but now, many of the logical functions that are performed on the ultrasonic signals can be digital, and hence, the conversion is preferred at an early stage in the signal-processing process. In this way, the receive beamformer 214 may receive a series of waveforms for separate acoustic lines in succession over time and process the data in a pipeline-processing manner. The receive beamformer 214 may combine the series of received waveforms to form a single acoustic line. To accomplish this task, the receive beamformer 214 may delay the separate echo waveforms by different amounts of time and then may add the delayed waveforms together, to create a composite digital RF acoustic line. The foregoing delay and sum beamforming process is well known in the art. Furthermore, the receive beamformer 214 may receive a series of data collections for separate acoustic lines in succession over time and process the data in a pipeline-processing manner.

The output of the receive beamformer 214 may be coupled to a RF filter 216. The RF filter 216 may take the form of a bandpass filter configured to remove undesired high-frequency out-of-band noise from the plurality of waveforms. The output of the RF filter 216 may then be coupled to an I, Q demodulator 218 configured to receive and process digital-acoustic lines in succession. The I, Q demodulator 218 may comprise a local oscillator that may be configured to mix the received digital-acoustic lines with a complex signal having an in-phase (real) signal and a quadrature-phase (imaginary) signal that are ninety degrees out-of-phase from one another. The mixing operation may produce sum and difference-frequency signals. The sum-frequency signal may be filtered (removed), leaving the difference-frequency signal, which is a complex signal centered near zero frequency. A complex signal is desired to follow direction of movement of anatomical structures imaged in the object-under-test, and to allow accurate, wide-bandwidth amplitude detection.

Up to this point in the ultrasound echo-receive process, all operations can be considered substantially linear, so that the order of operations may be rearranged while maintaining substantially equivalent function. For example, in some systems it may be desirable to mix to a lower intermediate frequency or to baseband before beamforming or filtering. Such rearrangements of substantially linear processing functions are considered to be within the scope of this invention.

As illustrated in FIG. 4, a plurality of signal processors may be coupled to the output of the I, Q demodulator 218. For example, a B-mode processor 222, and a Doppler processor 224 may be introduced at the output of the I, Q demodulator 218. Both the B-mode processor 222 and the Doppler processor 224 may comprise a suitable species of random-access memory (RAM) and may be configured to receive the filtered digital-acoustic lines. The acoustic lines can be defined within a two-dimensional coordinate space. The B-mode processor 222 and the Doppler processor 224 may be configured to accumulate acoustic lines of data over time for signal manipulation. As also illustrated in FIG. 4, the ultrasound-electronics system 202 may further comprise a two-dimensional/three-dimensional scan converter 226 to convert the data as stored in the RAM of either image-mode processor to produce pixels for display. The two-dimensional/three-dimensional scan converter 226 may process the data in the RAM once an entire data frame (i.e., a set of all acoustic lines in a single view, or image/picture to be displayed) has been accumulated by the RAM. For example, if the received data is stored in RAM using polar coordinates to define the relative location of the echo information, the two-dimensional/three-dimensional scan converter 226 may convert the polar coordinate data into rectangular (orthogonal) data capable of raster scan via a raster-scan capable image processor.

Having completed the transmitting, receiving, echo recovery, and two-dimensional image-signal processing functions, the ultrasound-electronics system 202 may forward the echo-image data information to a video-electronics system 205 as illustrated in FIG. 4. The video-electronics system 205 may receive the echo-image data from the ultrasound-electronics system 1, where the echo image data may be forwarded to a dual two-dimensional/three-dimensional image processor 228. The two-dimensional/three dimensional image processor 228 may be designed to receive the echo-image data information and may be configured to raster scan the image information. The two-dimensional/three-dimensional image processor 228 may be configured to output picture elements (e.g., pixels) for storage in an image-memory device 230 and/or for display via a suitable-display monitor 232. The image-memory device 230 may take the form of a digital-video disk (DVD) player/recorder, a compact-disc (CD) player/recorder, a video-cassette recorder (VCR) or other various video-information storage devices. As is known in the art, the image-memory device 230 permits viewing and or post data-collection image processing by a user/operator in other than real-time.

A display device in the form of a display monitor 232 may be in communication with the image memory 230 as illustrated in FIG. 4. In an alternative embodiment (not shown) the two-dimensional/three-dimensional image processor 228 may supply pixel data to both an image memory 230 and the display monitor 232. The display monitor 232 may be configured to receive the pixel data from either the image memory 230 and or the two-dimensional/three-dimensional image processor 228 and drive a suitable screen for viewing of the ultrasound image by a user/operator.

User-Identified Spot Three-Dimensional Imaging

Figure 1:
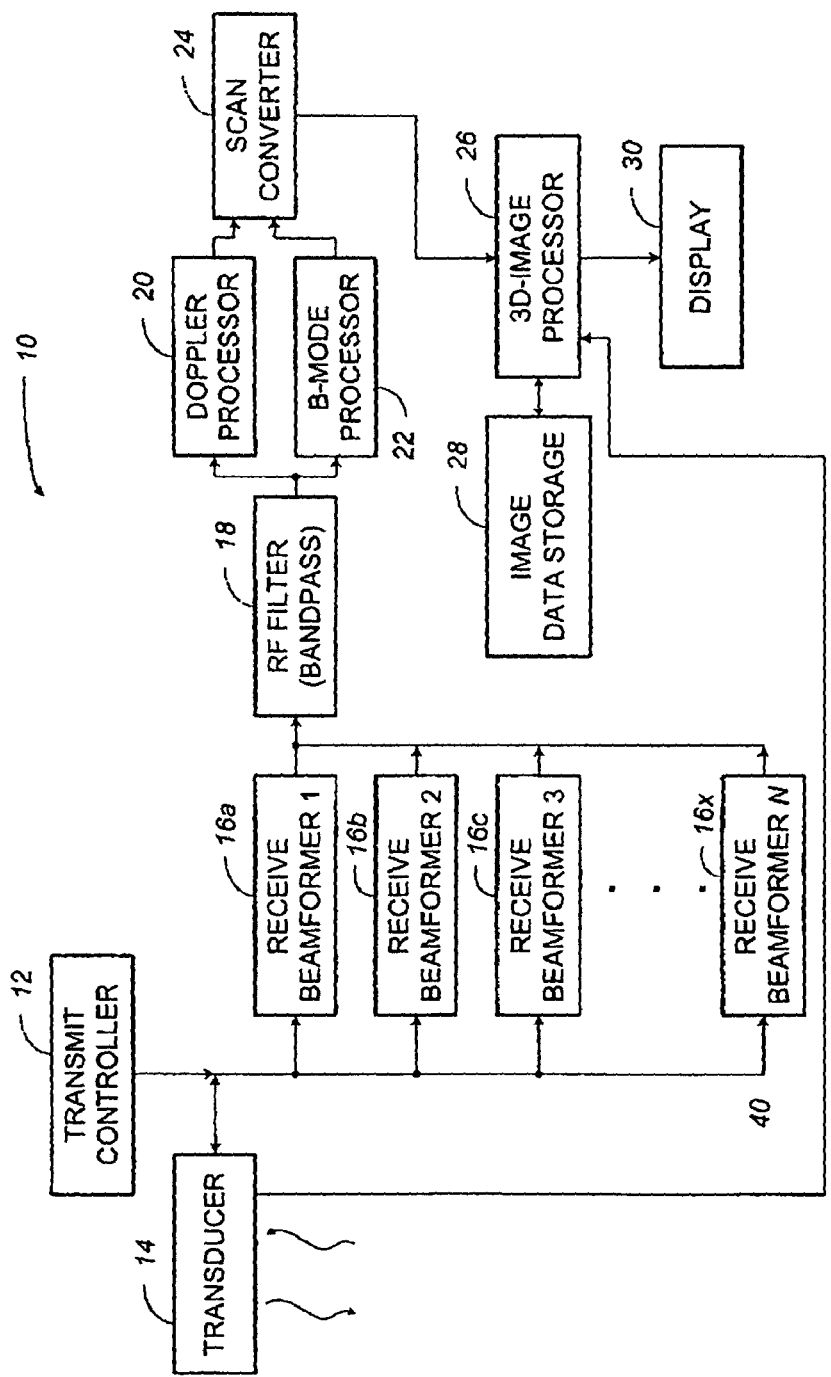
FIG. 1 is a block diagram of a prior-art three dimensional ultrasound-imaging system.
Figure 5:
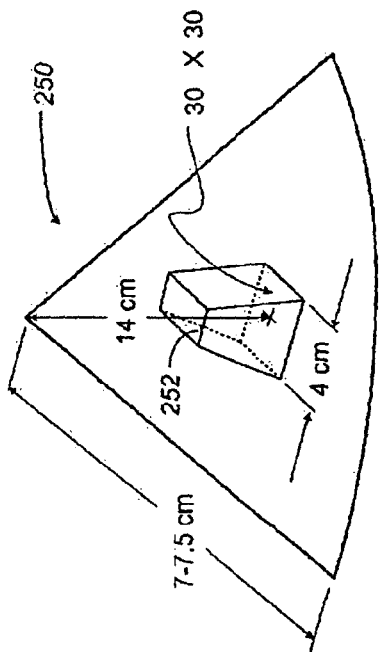
FIG. 5 is a schematic illustrating an approach to three-dimensional imaging as might be practiced by the three-dimensional ultrasound-imaging system of FIG. 4.
Figure 2:
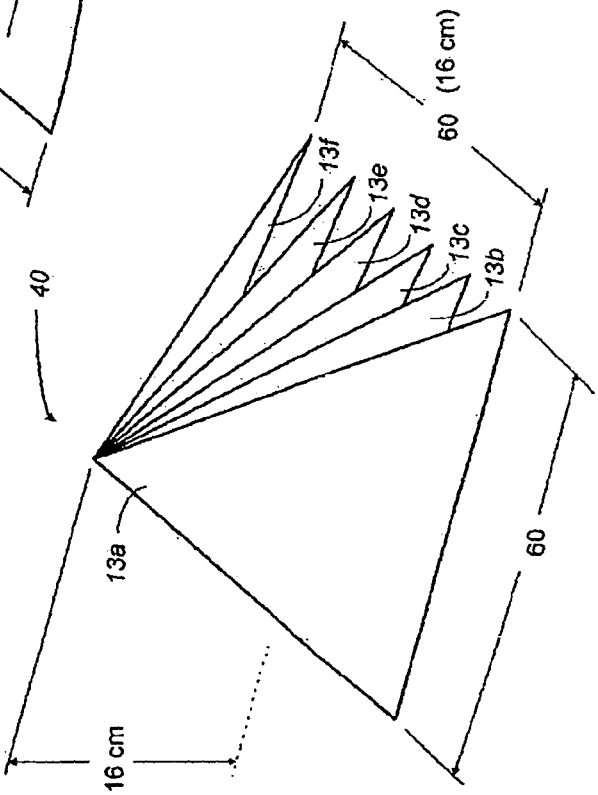
FIG. 2 is a schematic illustrating a prior-art approach to three-dimensional imaging as might be practiced by the prior-art three-dimensional ultrasound-imaging system of FIG. 1.

Having described the architecture and operation of the ultrasound-imaging system 200 of FIG. 4, attention is briefly directed to FIG. 5, which illustrates a display image 250 that may be produced by the ultrasound-imaging system 200 of FIG. 4. In this regard, a three-dimensional perspective view of an object 252 is presented within the display image 250. By directing a limited number of transmit-scan lines with a transducer array that produces a narrower beamwidth, the area of the largest face of the three-dimensional object 252 observed within the display image 250 will be reduced in comparison with the volume that may be observed with the prior-art three-dimensional imaging system 10 (FIG. 1). For example, a 30° by 30° two-dimensional scan pattern may be used to reproduce the object 252, which may have a maximum depth of approximately 14 cm. It will be appreciated that a reduction in the breadth of the two-dimensional scan pattern in both azimuth and elevation will result in a decrease in image-acquisition time. As a result the maximum frame rate may be increased to a rate suitable for real-time imaging of a VOI.

As will be explained in further detail below, an ultrasound-imaging system 200 in accordance with the present invention may use a narrower transmit beamwidth coupled with user-directed information to identify a location within a VUO and a suitable algorithm for varying the relative spacing of transmit planes across a focused region-of-interest to improve the rate of acquisition and or simulate perspective in a rendered image of an object. The ultrasound-imaging system 200 uses a 4× parallel operation (i.e., 1 transmit for 4 receive beams) with a transmit beam having an approximate span of 2°×2°. Each of the 4 receive beams may be configured such that they are applied with approximately a 1° separation within the transmit beam.

Figure 3:
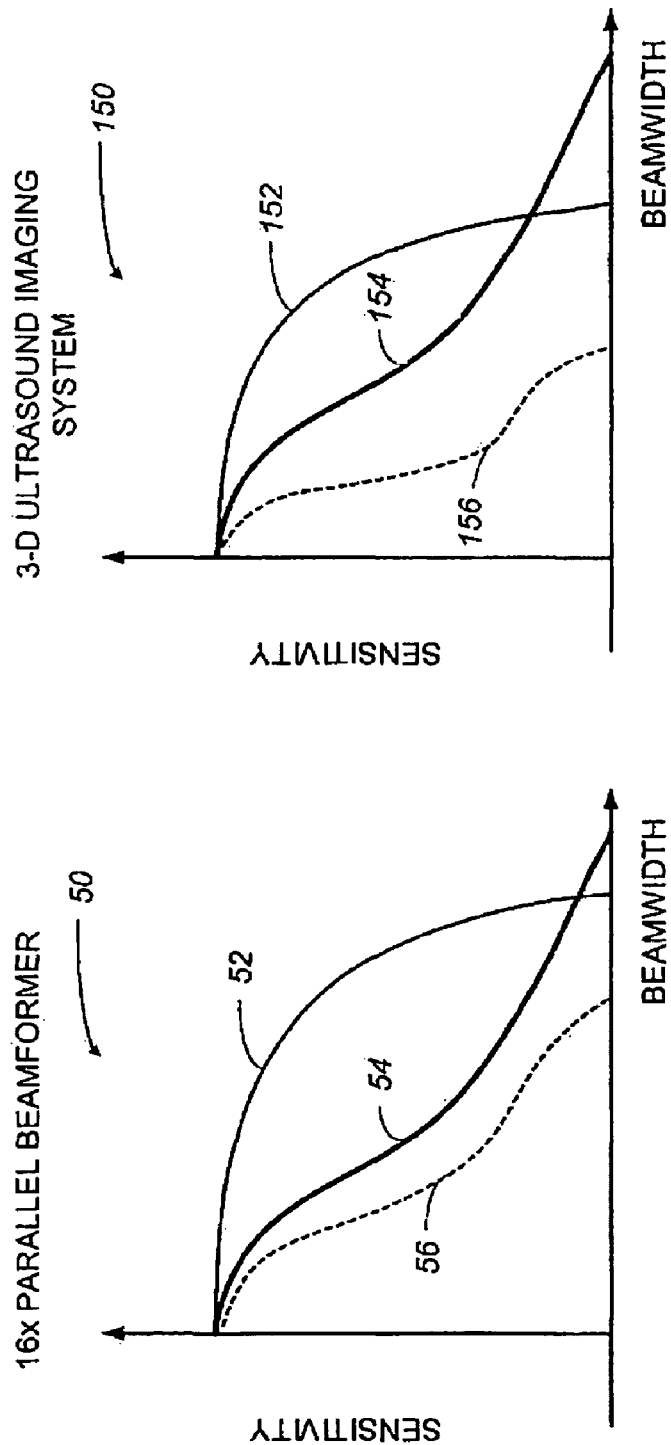
FIG. 3 is a plot illustrating transmit and receive ultrasound-signal sensitivity versus beamwidth as may be attainable by the prior-art three-dimensional ultrasound-imaging system of FIG. 1.

In this regard, the expected-performance characteristics 150 of the ultrasound-imaging system 200 of FIG. 4, as illustrated in FIG. 6, may be compared with the performance characteristics previously introduced in relation to a prior-art three-dimensional ultrasound-imaging system 10 (see FIG. 3). As illustrated in FIG. 6, a transmit plane 152, a receive plane 154, and a round-trip sensitivity 156 versus transmitted beamwidth may behave as shown. The ultrasound-imaging system 200 of FIG. 4 may use a narrower beamwidth to produce a similar receive plane 154 function. In addition, the narrower beamwidth may result in a significantly narrower round-trip sensitivity 156 (i.e., it is more tightly focused) when compared with the round-trip sensitivity 56 that may be observed with a prior-art three-dimensional ultrasound-imaging system 10 using a significantly wider transducer beamwidth.

As illustrated in FIG. 7, the transducer 212 in communication with the ultrasound-electronics system 202 of FIG. 4 may be presented with a plurality of electrical signals varied in time that may be directed at the various transducer elements on the transducer face 213 such that a plurality of steered or focused-transmit beams 215 emanate from the transducer face 213 in a controllable manner.

An ultrasound-imaging system 200 in accordance with the present invention may reduce the number of sample points collected to form an ultrasound image by varying the distance between sample points on the sampling grid 240 as a function of the transmit beam 215 (FIG. 7) deflection. Since the transmit and receive beamwidths nominally broaden as the beam is steered farther aware from the "bore" sight of the transducer, a coarsening of the distance between scan lines as the scan lines are steered further from the bore sight, permits the ultrasound-imaging system 200 of the present invention to maximize frame rate while still maintaining optimal-image quality.

Having briefly described transmit-beam steering in the context of FIG. 7, reference is now directed to FIGS. 8 through 13, which illustrate a series of possible image displays that may be generated by the ultrasound-imaging system 200 of FIG. 4. In this regard, a standard two-dimensional imaging-mode display 260 may be presented by the ultrasound-imaging system 200 (FIG. 4) as illustrated in FIG. 8. As shown in FIG. 8, the two-dimensional imaging-mode display 260 may assume a somewhat conical format. The general boundaries of the two-dimensional imaging-mode display 260 illustrated in FIG. 8 are the direct result of the time difference associated with ultrasonic reflections that originate with objects having a greater depth within the volume-under-test. It will be appreciated by those skilled in the art that this two-dimensional display mode is common to commercially available ultrasound-imaging systems. The general boundaries of the two dimensional imaging-mode display 260 confine the object and provide a perspective frame to assist an operator in deciphering the image information. As also illustrated in FIG. 8, the display electronics associated with the ultrasound-imaging system 200 of FIG. 4 may supply a user-selectable mode switch or push-button 262, herein labeled "3D" to indicate to an operator that a "3D" imaging mode is available when viewing an object-of-interest in a standard two-dimensional viewing mode.

Upon selecting the "3D" labeled switch or push-button 262, the video-electronics system 205 (FIG. 4) may work together with the ultrasound-electronics system 202 (FIG. 4) to present a standard two-dimensional imaging-mode display 270 as illustrated in FIG. 9. As shown in FIG. 9, the two-dimensional imaging-mode display 270 may comprise a user-selectable (in size and relative position) positioning window 272 to identify a user-desired imaging-focal point within the VUO. As also illustrated in FIG. 9, the display electronics associated with the ultrasound-imaging system 200 of FIG. 4 may supply a plurality of user-selectable mode switches or push-buttons 274, 276, and 278, herein labeled "POS.," "SIZE," and "3D," respectively. The plurality of user-selectable mode switches or push-buttons 274, 276, and 278 may be operable such that only one of the user-selectable input modes (i.e., POS. or SIZE) may be active at any given time. For example, if the operator selects the "POS." switch or push-button 274, the ultrasound-electronics system 202 (FIG. 4) may enter a user-input mode where image processing remains on hold until the operator enters a relative position that may be defined by the center of the user-selectable-positioning window 272 within the display 270. This operation may be accomplished by a keyboard, a mouse, or other user-operable input device together with appropriate software to accomplish the task.

By way of further example, if the operator continues by selecting the "SIZE" switch or push-button 276, the ultrasound-electronics system 202 (FIG. 4) may enter a second user-input mode where the size of the user-selectable positioning window 272 may be adjusted by an operator via a suitably configured user-input device (not shown). In response to various user directed inputs, the user-selectable positioning window 272 may be updated on the display 270 to indicate to an operator the present position and size of a user-defined imaging-focal point or focal plane. It is significant to note that the user-defined imaging reference may take the form of a frustum reference that may be later adjusted in depth or relative distance from a viewer's perspective within the VUO.

In this regard, reference is now directed to FIG. 10, which illustrates a three-dimensional imaging-mode display 280 as may be presented by the ultrasound-imaging system 200 (FIG. 4). As shown in FIG. 10, the three-dimensional imaging-mode display 280 may focus in on a user-identified portion of a two-dimensional image as explained hereinabove with reference to the schematic of FIG. 9. As illustrated in FIG. 10, the general boundaries of the three-dimensional imaging-mode display 280 may reflect only a small portion of the two-dimensional image used to identify a target portion of the VUO. As further illustrated in FIG. 10 a VOI 282 within the larger VUO (FIG. 9) may be rendered by the video-electronics system 205 (FIG. 4) such that the VOI 282 resembles a truncated pyramid. The target VOI 282 displayed within the three-dimensional imaging-mode display 280 may comprise a frustum-reference frame 284 that may be user adjusted or scanned across a user-defined depth of the target region. In a preferred embodiment, once button 278 is selected (FIG. 9), the ultrasound-imaging system 200 displays the VOI 282 as a rendered image. Since the ultrasound-imaging system 200 performs "volume rendering," the VOI 282 may appear as a three-dimensional surface-like rendering to the user, which can be rotated as the data is being acquired in real-time. It may be possible, in a "post-acquisition mode" (i.e., no longer acquiring live data) to manipulate the previously acquired imaging data to slice the small-spot volume (i.e., the VOI) to produce a single tomographic slice from this sub-volume of the VUO.

Having generally introduced the various display modes and user-selectable target position and display-mode options associated therewith with regard to the schematics illustrations in FIGS. 8 through 10, reference is now directed to FIGS. 11 through 13, which illustrate the use and operation of a frustum-reference frame 284 in three-dimensional imaging of a human organ such as the heart. In this regard, FIGS. 11 through 13 present schematic views of possible ultrasound-imaging displays that may be produced by the ultrasound-imaging system 200 of FIG. 4. A first imaging mode is presented in the schematic illustrated in FIG. 11. As shown in FIG. 11, a two-dimensional imaging-mode display 290 such as that previously presented and described with regard to the schematic of FIG. 8 may be generated by the ultrasound-imaging system 200 of FIG. 4 when an operator appropriately configures the system to observe a cross-sectional slice of a human heart. As illustrated in FIG. 11, an operator can adjust the various imaging parameters and direct the ultrasound-imaging system 200 of FIG. 4 such that a portion of an organ-of-interest (e.g., a human heart or VOI 282) within a larger VUO may be rendered on a display monitor 232 (FIG. 4).

As previously described with regard to FIG. 8, the display electronics associated with the-ultrasound-imaging system 200 of FIG. 4 may supply a user-selectable mode switch or push-button 262, herein labeled "3D" to indicate to an operator that a "3D"-imaging mode is available when viewing an object in a standard two-dimensional viewing mode, such as the cross-sectional viewing mode depicted in FIG. 11. Upon selecting the "3D" labeled switch or push-button 262, the video-electronics system 205 may work together with the ultrasound-electronics system 202 (FIG. 4) to present a standard three-dimensional imaging-mode display 300 as illustrated in FIG. 12. As shown in FIG. 12, a three-dimensional-imaging mode based on a frustum-reference-frame 284 or alternatively the cross-sectional two-dimensional image 290 illustrated in FIG. 11 may be used to reference a three-dimensional sub-volume display 300. For example, the three-dimensional sub-volume display 300 may comprise a three-dimensional rendering based on the cross-section of a human heart as illustrated in FIG. 11. As also illustrated in FIG. 12, the display electronics associated with the ultrasound-imaging system 200 of FIG. 4 may supply a plurality of user-selectable mode switches or push-buttons 302, 288 herein labeled "FLIP" and "2D," respectively.

The user-selectable mode switches or push-buttons 302, 288 may be operable as follows. If the operator selects the "FLIP" switch or push-button 302, the ultrasound-electronics system 202 (FIG. 4) may enter a display mode wherein the observation direction of the view is adjusted by 180°. This operation may be accomplished in response to the operator selecting the "FLIP" switch or pushbutton 302. If the operator were to proceed by selecting the "2D" switch or button 288, the ultrasound-electronics system 202 (FIG. 4) may return to the two-dimensional cross-sectional view as illustrated in FIG. 11 or in the alternative, a separate two-dimensional reference view.

If the three-dimensional sub-volume view mode of FIG. 12 is presently displayed and an operator selects the "FLIP" switch or pushbutton 302 as previously described, the ultrasound imaging electronics 202 (FIG. 4) may respond by rendering a three-dimensional imaging-mode display 310 as is illustrated in FIG. 13. As shown in FIG. 13, the three-dimensional imaging-mode display 310 may "flip" or adjust the viewing reference point by 180° to display a front portion of a VOI. Three-dimensional display modes designated to illustrate a VOI may be based upon a standard two-dimensional imaging mode. It is significant too note that the Doppler-mode and B-mode processors 222, 224 presented in FIG. 4 are referenced by way of example only to describe the operation of the ultrasound-imaging system 200 in accordance with the present invention. All two-dimensional imaging modes are within the scope of the present invention.

It is further significant to note that each of the representative ultrasound-imaging system 200 sample displays illustrated in FIGS. 8 through 13 may further comprise various image-source information as may be desired to easily identify the subject matter of the image, the image-viewpoint, the reference-imaging mode, a three-dimensional imaging mode, etc. In this regard, the various ultrasound displays illustrated in FIGS. 8 through 13 may comprise alphanumeric information in the form of patient identifiers, date and time identifiers, scanning parameters, and the like, in addition to the aforementioned imaging identifiers. Furthermore, the various ultrasound-imaging system 200 displays illustrated in FIGS. 9 through 13 may further comprise other indicators such as a frustum reference 284 superimposed over the VOI 282 to further identify the subject matter rendered in the various displays.

Figures 14A, 14B:
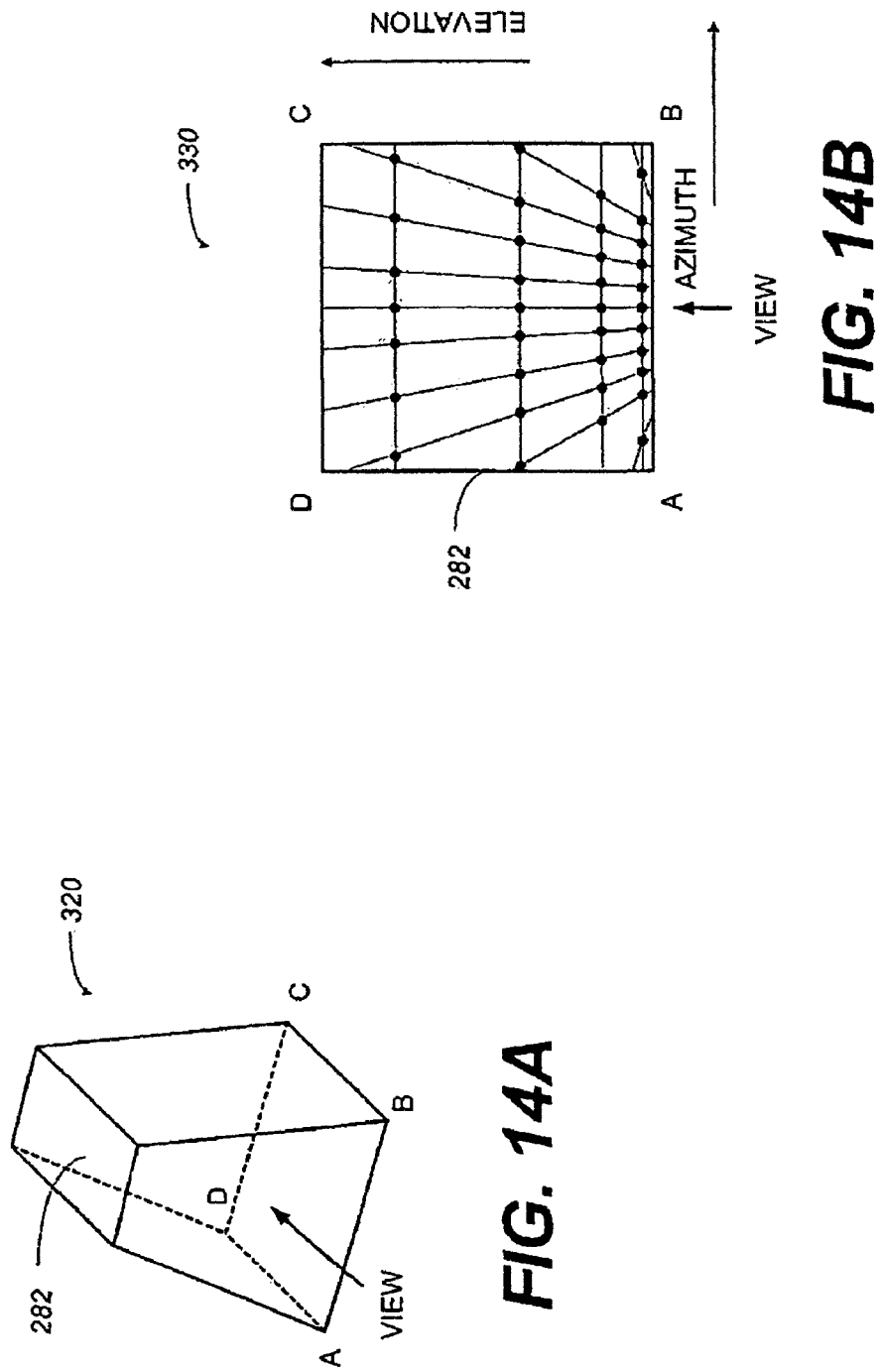
FIGS. 14A and 14B introduce a perspective view and a two-dimensional plot illustrating an operator-selectable view-point and the varying of transmit-scan lines to improve frame rate as may be implemented by the three-dimensional ultrasound-imaging system of FIG. 4.

Having generally introduced and described the various display modes and user selectable display-mode options associated therewith with regard to the schematic illustrations in FIGS. 11 through 13, reference is now directed to FIGS. 14A and 14B, which illustrate the use and operation of a user-identified view source along with varying scan lines in three-dimensional imaging. In this regard, FIG. 14A presents a perspective view 320 of a VOI 282 as observed from a view source or orientation generally indicated by a directional arrow labeled "VIEW." It is important to note that the ultrasound-imaging system 200 of FIG. 4 may permit an operator to interactively select a user-defined view source that defines a direction of view. As further illustrated in FIG. 14A, a three-dimensional rendering of a VOI 282 may comprise a base area identified by points A, B, C, and D. As revealed in the two-dimensional transmit-scan line plot generally identified with reference numeral 330, the base area of the three-dimensional sub-volume may relate to the four corners of the two-dimensional transmit-scan line plot 330, which illustrates a method of varying scan lines both in azimuth and elevation dimensions to more efficiently acquire the image information within VOI 282 (FIG. 14A).

In accordance with the principles of the present invention, a plurality of transmit beams emitted from an operating plane identified by the face of a transducer 212 element array or alternatively from a frustum-reference frame 284 defining the boundaries of a VOI 282 can be focused or directed in the azimuth dimension by actuating transducer elements in a set of grouped-transducer elements at slightly different times. Through such timed ultrasonic-pulsed transmissions, the plurality of transmit beams can be focused to a desired point or steered in a desired direction. Similarly, the transmitted beam may be focused or steered in the elevation direction by actuating transducer elements in a set of grouped-transducer elements at slightly different times. A plurality of steered-transmitted ultrasonic beams that vary in the elevation direction as defined by the face of a transducer element array may be used to generate a plurality of ultrasound-image echoes.

For example, a plurality of transmit-scan lines may be generated and transmitted using the transducer 212 (FIG. 4) such that the plurality of transmit-scan lines are offset radially from a direction substantially perpendicular from the face of the various transducer elements 215 (FIG. 7) that compose the transducer array. As shown in FIG. 14B, the degree or magnitude of the angular offset from 90° (i.e., a perpendicular transmit-scan line direction) may vary in relation to the distance the transmit-scan line source is offset from a predetermined transmit-scan line source on the transducer-element array. Furthermore, various ultrasound-echo sample points represented by the solid dots at the intersection of the varied transmit-scan lines and the plurality of horizontal lines may be adjustable in relation to user-selected imaging parameters. By reducing the number of ultrasound-transmit lines used to acquire and render a three-dimensional VOI 282 in concert with a narrower transmit beamwidth, the ultrasound-imaging system 200 of FIG. 4 may provide a more detailed multi-dimensional image at an improved frame-acquisition rate than what could be acquired using a wider transmit beamwidth with a prior-art three-dimensional parallel beamforming architecture using significantly more beamforming channels.

It is significant to note that the exemplar transmit-scan line pattern illustrated in FIG. 14B introduces two distinct degrees of freedom. The first degree of freedom is exemplified by the variable spacing in azimuth to achieve a perspective-like view. As long as the transmit-scan lines are variably spaced in azimuth, then the elevation pitch (i.e., the distance plane to plane) may be constant (i.e., periodic). Alternatively, even without variable transmit-scan line spacing in azimuth to achieve a perspective view, it may be desirable to vary the spacing in elevation. Volume rendering is more dominated by "frontal" structures because they tend to obscure more distal structures. Hence, it is desirable to fire higher-resolution lines through those portions of the VOI, which have the greatest impact on image quality.

Furthermore, as illustrated in the various views of FIGS. 15A through 15C a multi-dimensional image processor such as the two-dimensional/three-dimensional image processor 228 of the ultrasound-imaging system 200 of FIG. 4 may be configured to vary transmit-scan lines when acquiring imaging information from an insonified object. As previously described in relation to the transmit-scan line pattern of FIG. 14B, transmit-scan line spacing may be varied in both azimuth and in elevation to create rendered-object perspective and to provide greater image resolution on specific portions of an object-under-observation.

In this regard, FIG. 15A presents a modified perspective view 340 of a VOI 282 as observed from a view source generally indicated by a directional-arrow labeled, "VIEW." It is important to note that the ultrasonic-imaging system 200 of FIG. 4 may permit an operator to interactively select a user-defined view source that defines a direction-of-view. As further illustrated in FIG. 15A, a three-dimensional rendering of a VOI 282 may comprise a base area identified by points A, B, C, and D. As shown in FIG. 15A an inverse-perspective view may be created by directly increasing the relative distance between scanned points in an azimuth dimension as the depth from a view source increases.

FIG. 15B presents a transmit-scan line plot generally identified with reference numeral 350, as may be formed by the base area of the three-dimensional VOI 282 of FIG. 15A identified by corners A, B, C, and D. The two-dimensional transmit-scan line plot represents the base area of the VOI 282 of FIG. 15A as observed from a view source generally indicated by the directional-arrow labeled, "VIEW." As illustrated in FIG. 15B the two-dimensional transmit-scan line plot may comprise an object defined by a set of planes that are substantially parallel in both the azimuth and depth dimensions. In accordance with the principles of the present invention, a plurality of transmit beams emitted from an operating plane identified by the face of a transducer-element array can be focused or directed in the azimuth dimension to simulate perspective when the subsequently acquired echoes from the object 355 are later rendered by the display-electronics system 205 of the ultrasound-imaging system 200 of FIG. 4.

For examples a three-dimensional rendering of the object 355 may be generated by the ultrasound-imaging system 200 of FIG. 4 as illustrated by the base area of the VOI 282 as shown in FIG. 15C. In this regard, the plurality of transmit echoes or ultrasound-receive lines may be adjusted during an image-rendering process such that the image information associated with ultrasonic reflections emanating from an insonified object 355 identified by substantially parallel planes in both the azimuth and depth directions may appear as if in a perspective view when a three-dimensional image is prepared and presented on a display monitor 232 in communication with the ultrasound-electronics system 202 of FIG. 4.

Figure 16:
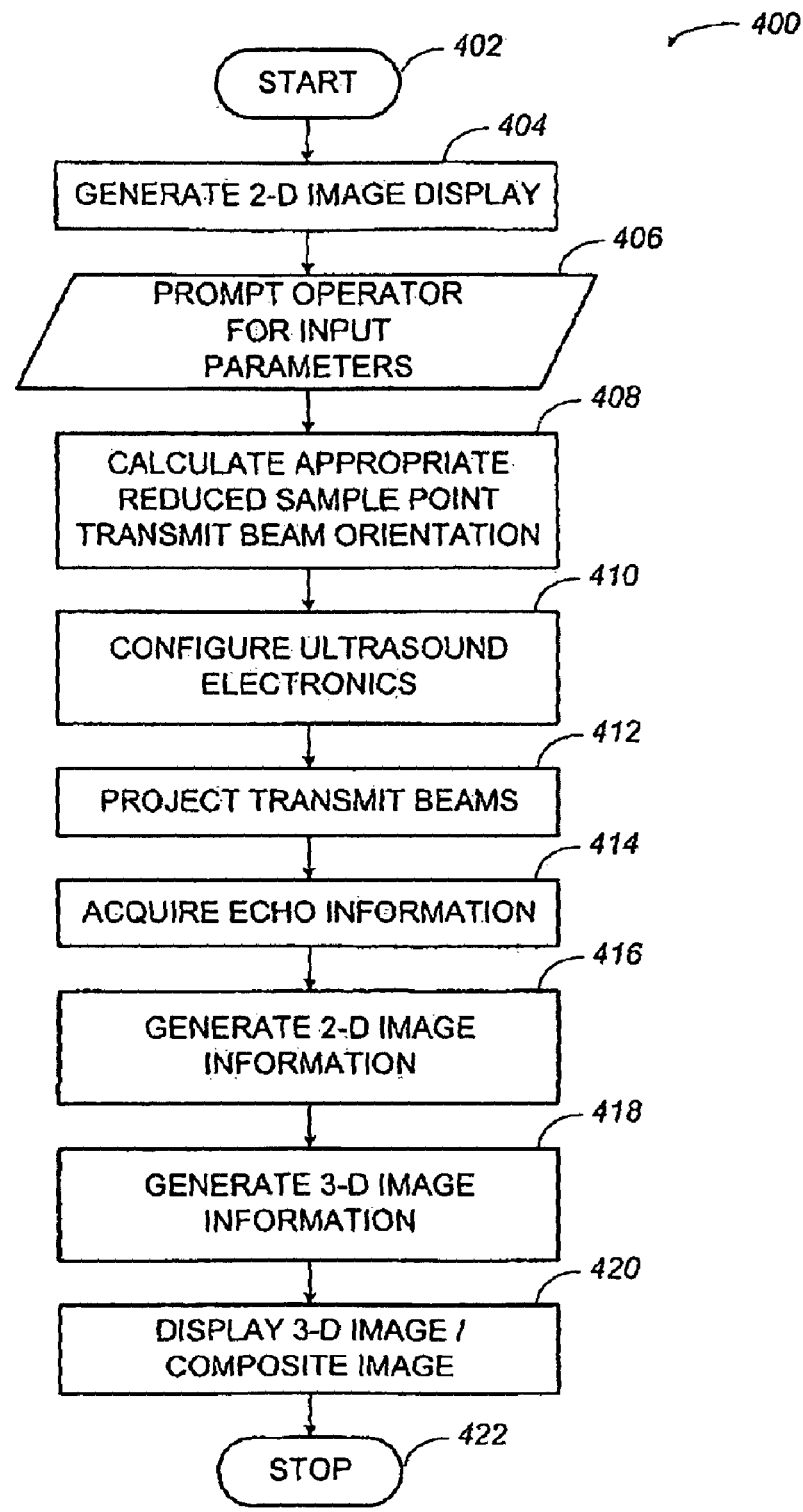
FIG. 16 is a flowchart illustrating a method for three-dimensional imaging as may be implemented by the ultrasound-imaging system of FIG. 4.

Reference is now directed to FIG. 16, which illustrates a flowchart describing a method for three-dimensional imaging that may be implemented by the ultrasound-imaging system 200 of FIG. 4. As illustrated in FIG. 16, a method for three-dimensional imaging 400 in accordance with the present invention may begin with step 402, labeled "START." First, a two-dimensional image may be generated and displayed as illustrated in step 404. As previously described, the two-dimensional image may be generated using a standard ultrasound-imaging-mode. For example, a B-mode image or a Doppler-mode image may be generated and displayed. Using the two-dimensional image generated and displayed in step 404 as a guide, the operator may be prompted for various three-dimensional imaging-input parameters as shown in step 406.

Having collected the necessary reference parameters in step 406, the method for three-dimensional imaging 400 may proceed by calculating an appropriate reduced sample-point transmit-beam orientation and scan sequence, as shown in step 408, in response to the user-selectable input parameters entered in step 406. Next, the method for three-dimensional imaging 400 may configure the ultrasound-electronics system 202 (FIG. 4) in accordance with the transmit-beam orientation and scan sequence as illustrated in step 410. The method for three-dimensional imaging 400 may proceed with step 412 where the ultrasound-electronics system 202 (FIG. 4) may work with transducer 212 to transmit the scan sequence derived in step 408 into a VOI 282.

Next, in step 414, the transducer 212 in communication with the ultrasound-electronics system 202 (FIG. 4) may acquire echo information as appropriate to derive image information from a VOI 282. Having acquired the necessary echo information in step 414, the method for three-dimensional imaging 400 may proceed to generate two-dimensional image information as shown in step 416. Next, in step 418, the two-dimensional image information generated in step 416 may be mathematically combined as required to generate three-dimensional imaging information from a plurality of two-dimensional images. It will be obvious to one skilled in the art that step 416 is optional, and that the generation of a three-dimensional image can be directly formed from the output of step 414. As illustrated in step 420, the method for three-dimensional imaging 400 may render and display a user-selected three-dimensional image.

In some embodiments, the method for three-dimensional imaging 400 may provide a user-selectable option at this point to superimpose the reference two-dimensional mode image with the user-directed three-dimensional image. Furthermore, other embodiments may provide the user with the option to display the 2D image next to (but not superimposed on) the 3D image. In addition, some embodiments of the method for three-dimensional imaging permit the operator to continuously select alternative-view points, imaging modes, view sizes, and the like while maintaining a suitable frame-acquisition rate to adequately view the various anatomical structures-of-interest in real time. Moreover, some embodiments of the method for three-dimensional imaging permit the operator to display multiple, live, 3D images. For example, it is possible to provide a display which simultaneously presents the same 3D information but from 2 or more view angles. Lastly, as illustrated in step 422, herein labeled "STOP," the method for three-dimensional imaging 400 may terminate.

It is significant to note that the software required to perform the functional activities illustrated in FIG. 4, or the mathematical combinations and data manipulations necessary to vary the transmit-scan lines within a sub-volume representing a portion of a larger VOI, as well as the data manipulations necessary to vary the receive echoes to simulate perspective of an object within the sub-volume as described in FIG. 16, may comprise an ordered listing of executable instructions for implementing logical functions. As such, the software can be embodied in any computer-readable medium for use by or in connection with an instruction-execution system, apparatus, or device, such as a computer-based system, processor-containing system, or other system that can fetch the instructions from the instruction-execution system, apparatus, or device and execute the instructions. In the context of this document, a "computer-readable medium" can be any means that can contain, store, communicate, propagate, or transport the program for use by or in connection with the instruction-execution system, apparatus, or device. The computer-readable medium can be, for example but not limited to, an electronic, magnetic, optical, electromagnetic, infrared, or semiconductor system, apparatus, device, or propagation medium.

More specific examples (a non-exhaustive list) of the computer-readable medium would include the following: an electrical connection (electronic) having one or more wires, a portable-computer diskette (magnetic), a random-access memory (RAM) (magnetic), a read-only memory (ROM) (magnetic), an erasable-programmable read-only memory (EPROM or Flash memory) (magnetic), an optical fiber (optical), and a portable compact-disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It should be emphasized that the above-described embodiments of the present invention are merely possible examples of implementations that are merely set forth for a clear understanding of the principles of the invention. Furthermore, many variations and modifications may be made to the above-described embodiments of the invention without departing substantially from the principles of the invention. All such modifications and variations are intended to be taught by the present disclosure, included within the scope of the present invention, and protected by the following claims.

Therefore, having thus described the invention, at least the following is claimed:

1. An ultrasonic diagnostic imaging system for two dimensional and three dimensional imaging comprising:
   an array transducer having a plurality of transducer elements extending in both the azimuth and elevation directions;
   a receive beamformer, coupled to receive echo waveforms from elements of the array transducer to produce beamformed echo signals from a volume under observation (VOU);
   a scan converter, coupled to receive beamformed echo signals from the beamformer, which operates to arrange echo-image data in a desired image format;
   a two-dimensional/three-dimensional image processor, responsive to echo image data to produce a two-dimensional or a three-dimensional image for display;
   a user control, operated in conjunction with a displayed two-dimensional or three-dimensional image produced by the image processor, which includes the following:
      a user-selectable control which operates, when a two-dimensional image of the VOU is displayed and a three-dimensional image is available for display, to display a three-dimensional image of the VOU separate from the two-dimensional image;
      a user-selectable control which operates, when a three-dimensional image of the VOU is displayed and a two-dimensional image is available for display, to display a two-dimensional cross-sectional image of the VOU separate from the three-dimensional image; and
      a user selectable control which operates to adjust the viewing reference point of a three-dimensional image by 180°; and
   a display responsive to the two-dimensional/three-dimensional image processor to display a two-dimensional or three-dimensional ultrasound image.

2. The ultrasonic diagnostic imaging system of claim 1, wherein the user selectable control which operates to adjust the viewing reference point of a three-dimensional image by 180° adjusts the observation direction of the view by 180°.

3. The ultrasonic diagnostic imaging system of claim 1, wherein the user control further comprises a user-selectable mode switch or push-button.

4. The ultrasonic diagnostic imaging system of claim 3, wherein the user-selectable mode switch or push-button further comprises a switch or button which is displayed on the display in association with an ultrasound image produced by the image processor.

5. The ultrasonic diagnostic imaging system of claim 4, wherein the user-selectable control which operates to display a three-dimensional image of the VOU is displayed on the display in association with a two-dimensional ultrasound image.

6. The ultrasonic diagnostic imaging system of claim 4, wherein the user-selectable control which operates to display a two-dimensional image of the VOU is displayed on the display in association with a three-dimensional ultrasound image.

7. The ultrasonic diagnostic imaging system of claim 4, wherein the user selectable control which operates to adjust the viewing reference point of a three-dimensional image by 180° is displayed on the display in association with a three-dimensional image.

8. The ultrasonic diagnostic imaging system of claim 7, wherein the user-selectable control which operates to display a two-dimensional image of the VOU is concurrently displayed on the display in association with the three-dimensional image.

* * * * *